(12) United States Patent
Hammond et al.

(10) Patent No.: US 12,429,479 B2
(45) Date of Patent: Sep. 30, 2025

(54) FLOW CYTOMETRY SYSTEMS AND METHODS FOR PRESENTING TWO-DIMENSIONAL DOT PLOT

(71) Applicant: IDEXX Laboratories Inc., Westbrook, ME (US)

(72) Inventors: Jeremy Hammond, Standish, ME (US); James Russell, North Yarmouth, ME (US); Dennis DeNicola, Windham, ME (US)

(73) Assignee: IDEXX LABORATORIES INC., Westbrook, ME (US)

( * ) Notice: Subject to any disclaimer, the term of this patent is extended or adjusted under 35 U.S.C. 154(b) by 167 days.

(21) Appl. No.: 18/111,187

(22) Filed: Feb. 17, 2023

(65) Prior Publication Data
US 2023/0266305 A1  Aug. 24, 2023

Related U.S. Application Data

(60) Provisional application No. 63/311,558, filed on Feb. 18, 2022.

(51) Int. Cl.
*G01N 33/50* (2006.01)
*G01N 15/1434* (2024.01)

(52) U.S. Cl.
CPC ..... *G01N 33/5094* (2013.01); *G01N 15/1434* (2013.01)

(58) Field of Classification Search
CPC .......... G01N 15/1434; G01N 33/5094; G01N 15/14; G01N 2015/1006; G01N 2015/1402; G01N 2015/1477
(Continued)

(56) References Cited

U.S. PATENT DOCUMENTS 6,524,858 B1   2/2003 Zelmanovic et al.
RE49,543 E  *  6/2023 Nitta ................. G01N 15/1434
                                                      250/591
(Continued)

OTHER PUBLICATIONS

Brems, M., "A One-Stop Shop for Principal Component Analysis" Towards Data Science (Apr. 2017), https://towardsdatascience.com/a-one-stop-shop-for-principal-component-analysis-5582fb7e0a9c.
(Continued)

*Primary Examiner* — Tri T Ton
(74) *Attorney, Agent, or Firm* — Carter, DeLuca & Farrell LLP

(57) ABSTRACT

A method for presenting flow cytometry data includes accessing sensed data of a flow cytometer used to sense optical responses from a sample including a plurality of components; estimating optical characteristic values, physical characteristic values, and counts of the plurality of components based on the sensed data; transforming at least some of the optical characteristic values, the physical characteristic values, or the counts, of at least one of the plurality of components, by at least one of rotating or translating, to provide transformed values; and presenting a two-dimensional (2D) dot plot base on the transformed values and based on at least some of the optical characteristic values, the physical characteristic values, and the counts, of the plurality of components. The 2D dot plot has a first axis corresponding to the optical characteristic values and a second axis corresponding to the physical characteristic values.

18 Claims, 8 Drawing Sheets

(58) Field of Classification Search
USPC .......................................................... 356/39
See application file for complete search history.

(56) References Cited

U.S. PATENT DOCUMENTS

| | | | | |
|---|---|---|---|---|
| 2007/0118297 | A1* | 5/2007 | Thayer | G01N 15/1459 |
| | | | | 702/21 |
| 2012/0245889 | A1 | 9/2012 | Zhu et al. | |
| 2015/0330888 | A1 | 11/2015 | Ramierz | |
| 2017/0322137 | A1* | 11/2017 | Feher | G01N 15/1429 |
| 2021/0080375 | A1* | 3/2021 | Nitta | G01J 3/2803 |

OTHER PUBLICATIONS

Surjikov, S.T., "MIEW Scattering" Thermopedia (Feb. 2011), https://www.thermopedia.com/content/956/.

International Search Report and Written Opinion issued in corresponding International Application No. PCT/US2023/013315, dated Jun. 23, 2023, pp. 1-2.

International Preliminary Report on Patentability issued in corresponding International Application No. PCT/US2023/013315, dated Aug. 20, 2024, pp. 1-6.

* cited by examiner

FLOW CYTOMETRY SYSTEMS AND METHODS FOR PRESENTING TWO-DIMENSIONAL DOT PLOT

CROSS-REFERENCE TO RELATED APPLICATIONS

This application claims the benefit of, and priority to, U.S. Provisional Patent Application No. 63/311,558, filed on Feb. 18, 2022, the entire contents of which are hereby incorporated herein by reference.

TECHNICAL FIELD

The present disclosure relates to flow cytometry systems and methods particularly for presenting flow cytometer data in a two-dimensional dot plot.

BACKGROUND

Flow cytometers measure components such as cells and particles in a solution, which move along a cuvette in front of a light source (e.g., laser) in a single file. Light from the light source is absorbed and scattered by the components in a manner that is dictated by associated stains in the solution as well as the size and morphology of the components.

SUMMARY

Sensor geometry and/or orientation to capture the scattered light signals plays a role in identifying the components in a sample. In general, the more light sensors there are, the more information can be obtained for identifying the components or presence of abnormalities in the components. Complexity in the analysis increases as the number of sensors increases. Further, presentation of data also becomes more complex as the number of the sensors increases. Thus, there is continuing interest in improving how to present data so that the data can be analyzed with greater ease.

The present disclosure relates to flow cytometry systems, methods, and instructions for analyzing and presenting flow cytometer sensor data in a dot plot so that data clusters corresponding to the components of a sample can be visually discernible in the dot plot.

In accordance with aspects of the present disclosure, a method for presenting flow cytometry data includes: accessing sensed data of a flow cytometer used to sense optical responses from a sample, where the sample includes a plurality of components; estimating optical characteristic values, physical characteristic values, and counts of the plurality of components based on the sensed data; transforming at least some of the optical characteristic values, the physical characteristic values, or the counts, of at least one of the plurality of components, by at least one of rotating or translating, to provide transformed values; and presenting a two-dimensional (2D) dot plot base on the transformed values and based on at least some of the optical characteristic values, the physical characteristic values, and the counts, of the plurality of components, where the 2D dot plot has a first axis corresponding to the optical characteristic values and a second axis corresponding to the physical characteristic values. The 2D dot plot includes data clusters corresponding to the plurality of components.

In embodiments of the method, the physical characteristic values are indicative of size and the optical characteristic values are indicative of scattering complexity.

In embodiments of the method, the sample includes white blood cells. The plurality of components include at least one of monocytes, lymphocytes, neutrophils, eosinophils, or basophils.

In embodiments of the method, the sample includes red blood cells and platelets.

In embodiments of the method, the plurality of components include at least one of red blood cells, reticulocytes, platelets, or white blood cells.

In embodiments of the method, the method further includes comparing the data clusters in the 2D dot plot with reference data clusters to determine presence of abnormality in the plurality of components.

In embodiments of the method, the data clusters corresponding to the plurality of components are substantially separated from each other in the 2D dot plot.

In embodiments of the method, the transforming includes magnifying at least some of the optical characteristic values or the physical characteristic values to provide at least some of the transformed values, where the magnifying results in at least some of the data clusters being separated or substantially separated in the 2D dot plot.

In embodiments of the method, the transforming includes rotating at least some of the optical characteristic values about at least one of the first axis or the second axis, to provide at least some of the transformed values, where the rotating results in at least some of the data clusters being separated or substantially separated in the 2D dot plot.

In embodiments of the method, the transforming includes translating at least some of the optical characteristic values or the physical characteristic values along at least one of the first axis or the second axis, to provide at least some of the transformed values, where the translating results in at least some of the data clusters being separated or substantially separated in the 2D dot plot.

In embodiments of the method, the transforming includes truncating the count of at least one of the plurality of components to provide at least some of the transformed values, where the truncating results in at least some of the data clusters being separated or substantially separated in the 2D dot plot.

In embodiments of the method, the transforming includes performing a principal component analysis on at least some of the optical characteristic values, the physical characteristic values, or the counts.

In accordance with aspects of the present disclosure, a system for presenting flow cytometry data includes a processor and a memory including instructions stored thereon. The instructions, when executed by the processor, cause the system to: access sensed data of a flow cytometer used to sense optical responses from a sample, where the sample includes a plurality of components; estimate optical characteristic values, physical characteristic values, and counts of the plurality of components based on the sensed data; transform at least some of the optical characteristic values, the physical characteristic values, or the counts, of at least one of the plurality of components, by at least one of rotation or translation, to provide transformed values; and present a two-dimensional (2D) dot plot based on the transformed values and based on at least some of the optical characteristic values, the physical characteristic values, and the counts, of the plurality of components, where the 2D dot plot has a first axis corresponding to the optical characteristic values and a second axis corresponding to the physical characteristic values. The 2D dot plot includes data clusters corresponding to the plurality of components.

In embodiments of the system, the physical characteristic values are indicative of size and the optical characteristic values are indicative of scattering complexity.

In embodiments of the system, the instructions, when executed by the processor, further cause the system to compare the data clusters in the 2D dot plot with reference data clusters to determine presence of abnormality in the plurality of components.

In embodiments of the system, the data clusters corresponding to the plurality of components are substantially separated from each other in the 2D dot plot.

In embodiments of the system, in performing the transforming, the instructions, when executed by the processor, cause the system to magnify at least some of the optical characteristic values and the physical characteristic values to provide at least some of the transformed values, where the magnifying results in at least some of the data clusters being separated or substantially separated in the 2D dot plot.

In embodiments of the system, in performing the transforming, the instructions, when executed by the processor, cause the system to rotate at least some of the optical characteristic values about at least one of the first axis or the second axis, to provide at least some of the transformed values, where the rotating results in at least some of the data clusters being separated or substantially separated in the 2D dot plot.

In embodiments of the system, in performing the transforming, the instructions, when executed by the processor, cause the system to translate at least some of the optical characteristic values or the physical characteristic values along at least one of the first axis or the second axis, to provide at least some of the transformed values, where the translating results in at least some of the data clusters being separated or substantially separated in the 2D dot plot.

In embodiments of the system, in performing the transforming, the instructions, when executed by the processor, cause the system to truncate the count of at least one of the plurality of components to provide at least some of the transformed values, where the truncating results in at least some of the data clusters being separated or substantially separated in the 2D dot plot.

In embodiments of the system, in performing the transforming, the instructions, when executed by the processor, cause the system to perform a principal component analysis on at least some of the optical characteristic values, the physical characteristic values, or the counts.

In accordance with aspects of the present disclosure, a processor-readable medium stores instructions which, when executed by a processor, causes performance of a method. The method includes: accessing sensed data of a flow cytometer used to sense optical responses from a sample, where the sample includes a plurality of components; estimating optical characteristic values, physical characteristic values, and counts of the plurality of components based on the sensed data; transforming at least some of the optical characteristic values, the physical characteristic values, or the counts, of at least one of the plurality of components, by at least one of rotating or translating to provide transformed values; and presenting a two-dimensional (2D) dot plot base on the transformed values and based on at least some of the optical characteristic values, the physical characteristic values, and the counts, of the plurality of components, where the 2D dot plot has a first axis corresponding to the optical characteristic values and a second axis corresponding to the physical characteristic values. The 2D dot plot includes data clusters corresponding to the plurality of components.

In embodiments of the processor-readable medium, the physical characteristic values are indicative of size and the optical characteristic values are indicative of scattering complexity.

Further details and aspects of exemplary aspects of the present disclosure are described in more detail below with reference to the appended figures.

DETAILED DESCRIPTION

The present disclosure provides flow cytometry systems and methods for separating data clusters from a flow cytometer and presenting the separated data clusters in a two-dimensional (2D) dot plot to permit even a non-expert to interpret data more easily. As used herein, the term "data cluster" refers to and includes data points, in a plot of any dimension, that are identifiable as belonging in a same group based on statistics, data science, and/or other mathematical or data metrics. Furthermore, the present disclosure provides ways to identify presence of abnormalities in the components in the sample.

Figure 1:
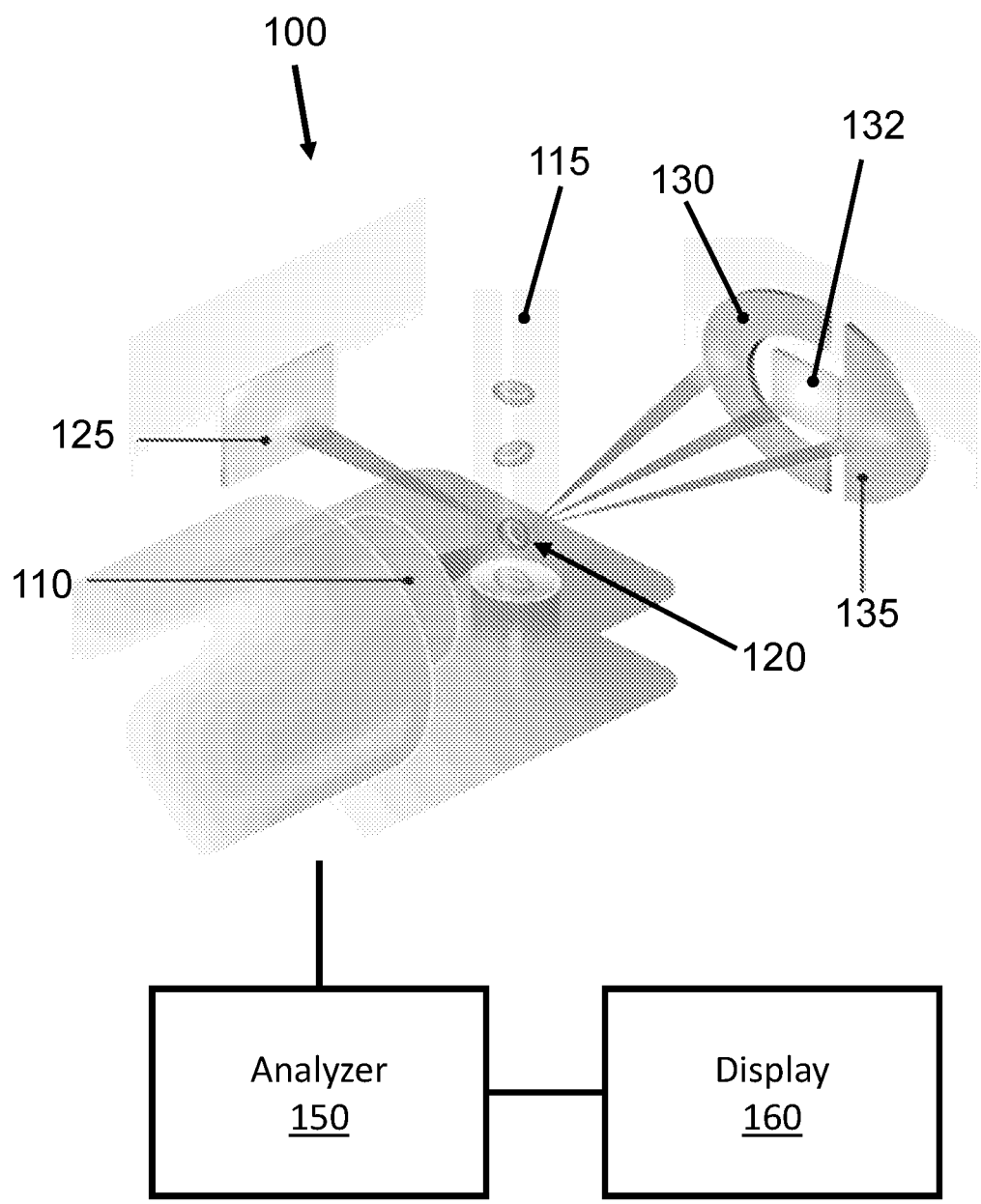
FIG. 1 is a schematic illustration of a flow cytometry system in accordance with aspects of the present disclosure.

FIG. 1 illustrates a schematic view of a flow cytometry system 100 according to aspects of the present disclosure. The flow cytometry system 100 includes a light source 110, an analyzer 150, and a display 160. The flow cytometry system 100, in embodiments, includes a cuvette 115 and light sensors 125, 130, 132, and 135. In operation, while a sample 120 (e.g., cells) moves forward in the cuvette 115, the light source 110 emits a beam of light that is oriented substantially orthogonally to the axial flow of the sample 120 through the cuvette 115. The beam of light emitted by the light source 110 has a central axis and, in embodiments, is a focused, narrow band beam (e.g., laser) or is a broadband beam. Aspects of a flow cytometer optical system are described in U.S. Pat. Nos. 6,320,656, 6,618,143, and 6,784,981, which are hereby incorporated by reference herein in their entirety. A brief description is provided below.

A portion of the beam from the light source 110 that impinges upon the sample 120 (e.g., the cells) flowing in the cuvette 115 is scattered at a right angle or substantially a right angle to the central axis of the beam of light (side scattered light, denoted as "SS") and is captured/sensed/measured by the side scatter sensor/detector 125. As used herein, the term "substantially a right angle" means and includes scattered light which is sensed by side scatter detector 125 even though it is not scattered at exactly a right angle. Any angle disclosed herein with respect to an axis means and includes such angle in any plane that includes the entire axis, without regard to the direction of the angle (e.g., 3° above an axis and 3° below an axis are both encompassed). As persons skilled in the art will understand, an infinite number of planes wholly include an axis, and an angle as used herein may be in any such plane.

A second portion of the beam from the light source 110 that impinges upon the cells flowing in the cuvette 115 is scattered at a much lower angle than 90° with respect to central axis of the beam of light. This scatter is termed "low angle forward scattered light" (FSL) and has an angle range, for example, of from approximately 1° to approximately 3° from the central axis of the beam from the light source 110, or has another angle range, which persons skilled in the art will recognize. In the illustrated embodiment, the light sensor 135 is oriented to capture the low angle forward scatter light oriented at approximately 1° to approximately 3° from the beam of the light source 110.

In the flow cytometry system 100, various other light signals may be detected or sensed and persons skilled in the art will understand such signals. In embodiments, such other light signals include extinction/axial light loss (EXT) (e.g., from 0° to approximately 0.5°), which is detected by the illustrated sensor 132, and high angle forward scattered light (FSH) (e.g., from approximately 4° to approximately 9°), which is detected by the illustrated sensor 130. Such light signals and angle ranges are exemplary, and other light signals and angles ranges will be understood by persons skilled in the art. In embodiments, a time metric known in the art as time-of-flight (TOF) may be measured and analyzed. As persons skilled in the art will recognize, TOF refers to the time that a sample (e.g., a cell) is interrogated by the beam from the light source 110. TOF may be measured based on EXT signals detected by sensor 132. The disclosure below may refer to one or more of SS, FSL, FSH, EXT, and TOF, as examples of light signals and metrics that can be used in accordance with aspects of the present disclosure. It is intended and will be understood that other flow cytometry light signals and metrics not expressly mentioned herein are also encompassed within the scope of the present disclosure.

The configuration of sensors 125, 130, 132, 135 in FIG. 1 is exemplary. In embodiments, the flow cytometry system 100 may be implemented by another configuration of sensors different from that shown in FIG. 1, and such other embodiments are contemplated to be within the scope of the present disclosure. The disclosure below may refer to the sensor configuration of FIG. 1 as an example of a configuration that may be used in accordance with aspects of the present disclosure. It is intended and understood that other sensor configurations are also encompassed within the scope of the present disclosure.

The light sensors 125, 130, 132, 135 provide electrical signals corresponding to light scattered by the components in the sample 120, and these electrical signals are analyzed to provide data indicative of SS, FSL, FSH, EXT, and TOF, among others. The data are collected and analyzed by the analyzer 150 and information based on the analyzed results are displayed on the display 160. As will be described in more detail below, the information displayed on the display 160 can be various plots that present the optical signals or metrics in a manner that permits a user to make assessments and diagnoses regarding the subject which provided the analyzed sample.

Figure 3:
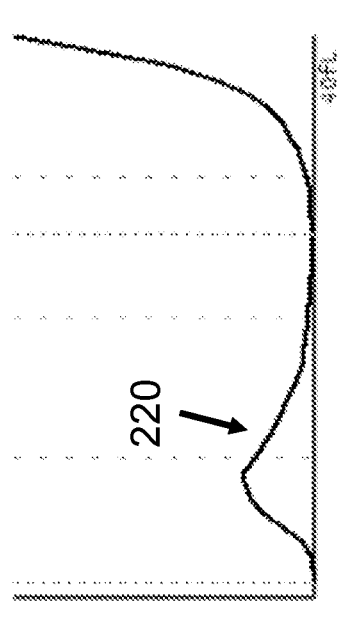
FIG. 3 is an example of another 1D graphical representation of data.
Figure 2:
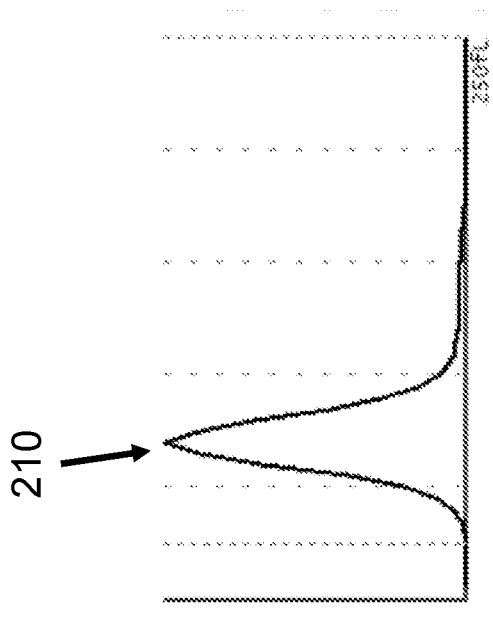
FIG. 2 is an example of a one-dimensional (1D) graphical representation of data.

FIGS. 2 and 3 show examples of one-dimensional plots of data or metrics derived from sensor measurements. For example, data from the sensors can be presented in one-dimension (1D), as a histogram shown in FIGS. 2 and 3, which are relatively easy to interpret. FIG. 2 shows an exemplary histogram 210 of scattered light signal from canine red blood cells, and FIG. 3 illustrates an exemplary histogram 220 of scattered light signal from canine platelets. Due to the different optical characteristics, the histograms are useful for identifying different components. The 1D histograms are beneficial in various circumstances. However, one difficulty with histograms arises where two or more populations overlap or superpose each other in one histogram, such that there is little information that suggests there is more than one population unless there are gross histogram morphology changes. The aspects, embodiments, and examples described in connection with FIG. 2 and FIG. 3 are exemplary, and it is contemplated that such aspects, embodiments, and examples may be implemented in connection with systems other than flow cytometry systems.

Figure 4:
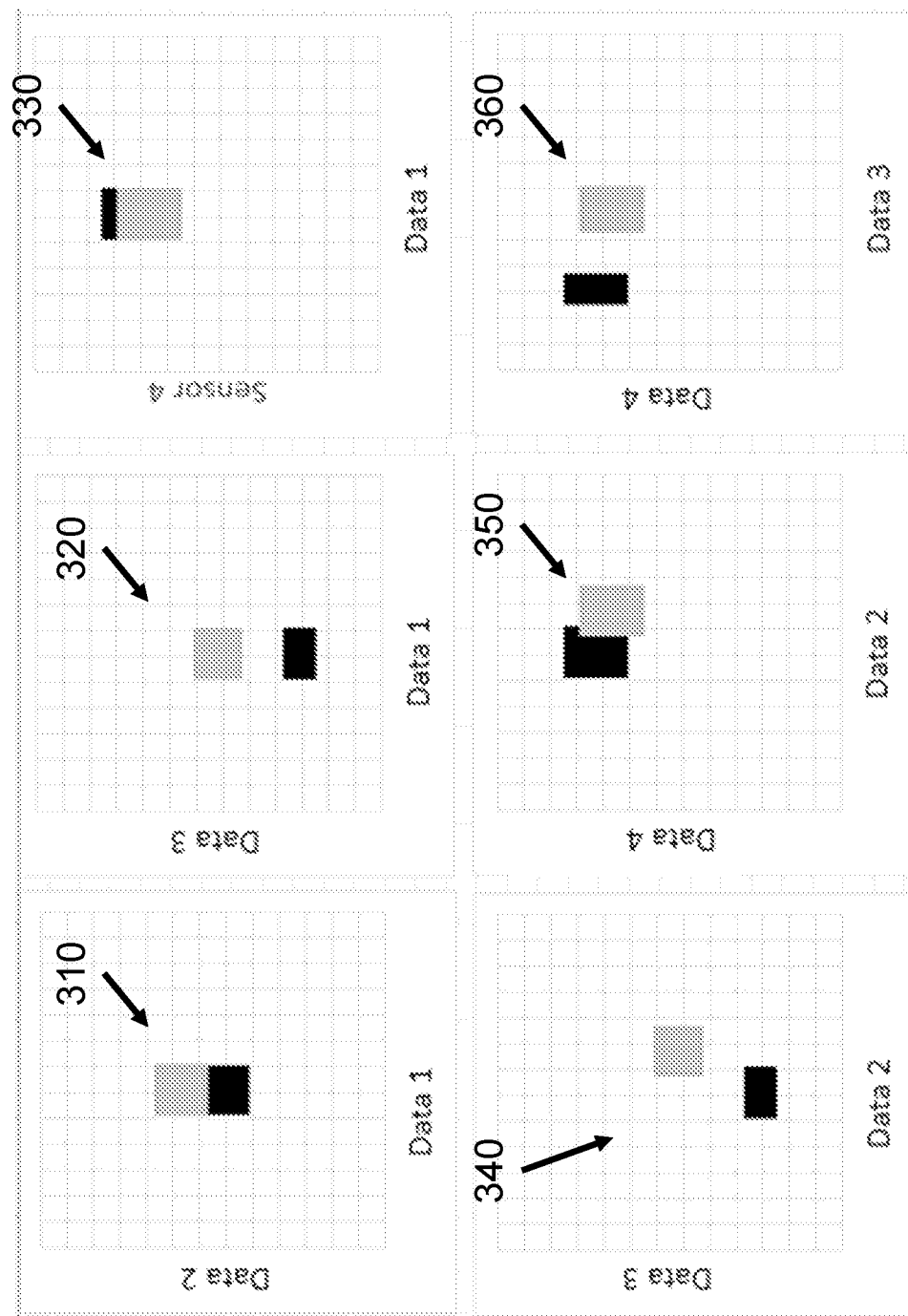
FIG. 4 shows 2D dot plots in accordance with aspects of the present disclosure.

FIG. 4 shows examples of two-dimensional plots of data or metrics obtained from sensor measurements. FIG. 4 will be described in connection with a flow cytometry system, but such description is exemplary and it is contemplated that the same aspects, embodiments, and examples may be implemented in connection with systems other than flow cytometry systems. As illustrated in FIG. 4, in circumstances in which the flow cytometry system 100 provides four data/metrics (e.g., SS, FSL, FSH, EXT, TOF), the analyzer 150 provides 2D plots using pairs of the four data/metrics. As an example, a single cell interrogated by the laser beam of the flow cytometry system produces values for SS, FSL, FSH, and EXT. This single interrogation would be a single dot in a 2D plot where the x-axis corresponds to one of the four data/metrics and the y-axis corresponds to another one of the four data/metrics. All pairings of four data/metrics results in six 2D representations 310-360. When a stream of cells is interrogated by the flow cytometry system and plotted, the result is a dot plot representing all of the cells that were interrogated. For illustrative purposes, black rectangles represent a data cluster corresponding to one component of a sample, and grey rectangles represent a data cluster corresponding to another component of the sample, which is different from the black rectangular data cluster. In actuality, the two clusters may not be presented in different colors, as the flow cytometry system would not have ex ante knowledge about which dot belongs to which component. Rather, as described below, a task of the presently disclosed technology is to present two clusters as visibly separate in order to assist users with visualizing the data to arrive at assessments and diagnoses.

As shown in FIG. 4, plots 320, 340, and 360 are 2D plots that show separation between two data clusters, whereas 2D plots 310, 330, and 350 show the two data clusters overlapping. Separated data clusters make it easier to identify the outline of discrete data clusters compared to overlapped data clusters. However, data clusters corresponding to different components of a sample may not always appear on 2D plots as separate clusters, like the plots shown in 320, 340, and 360. Rather, data clusters may appear on 2D plots as overlapping clusters, as shown in FIGS. 310, 330, and 350. As described below, machine learning or dimensional reduction, among other things, may be used to process 2D plots to distinguish or better present data clusters.

In accordance with aspects of the present disclosure, and with reference also to FIG. 1, the analyzer 150 may utilize machine learning algorithms to identify separate data clusters to identify components in the sample 120. As persons skilled in the art will understand, machine learning models such as support vector machines or neural networks, among others, may be trained by supervised training using labeled training data to classify data clusters to various components of a sample. Persons skilled in the art will understand how to implement such machine learning models.

In accordance with another aspect of the present disclosure, the analyzer 150 may utilize a dimensional reduction method, such as a principal component analysis (PCA), to provide better visual separation of data clusters. An example of using dimensional reduction (e.g., PCA) is described below with respect to FIGS. 5 and 6.

Figure 6:
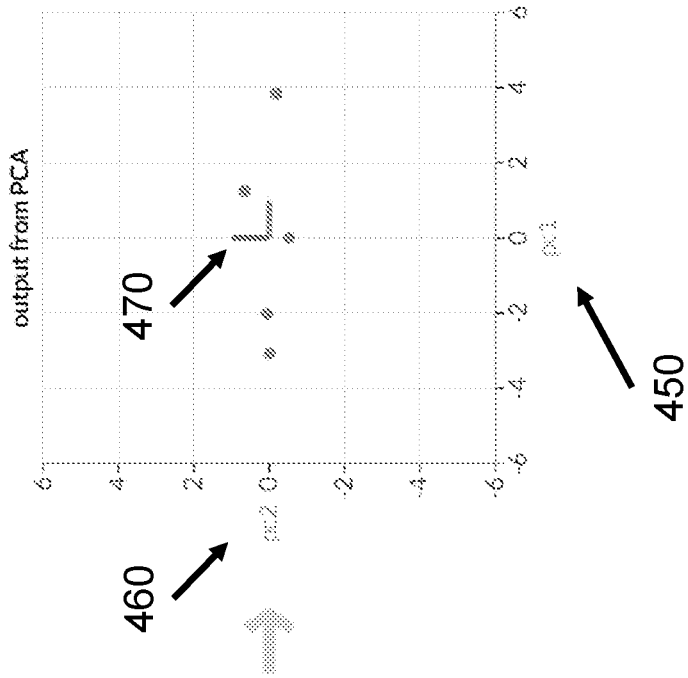
FIG. 6 is another 2D graph, which shows changes in the dot plot of FIG. 5 based on a principal component analysis in accordance with aspects of the present disclosure.
Figure 5:
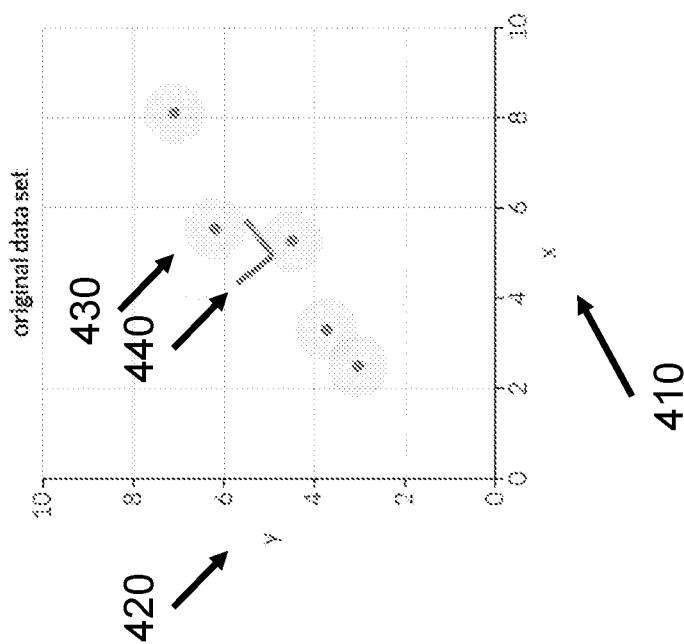
FIG. 5 is a two-dimensional (2D) graph, in accordance with aspects of the present disclosure.

FIGS. 5 and 6 illustrate an example of presenting a different view of data clusters by reducing the dimension of data samples 430 according to aspects of the present disclosure. FIG. 5 shows two orthogonal axes: an x-axis 410 and a y-axis 420. A plot of data samples 430 generally shows a straight-line distribution. FIG. 5 shows the two dimensional characteristics of the data samples 430, meaning that the y value increases as the x value increases and vice versa. Further, a small orthogonal indicator 440 is also shown in FIG. 4A to show linearity along the slope of the straight line.

After performing the PCA on the sample data 430, the greatest principal component can be calculated, and the data samples 430 can be transformed based on the greatest principal component and plotted as shown in FIG. 6. In other words, a new x-axis 450 and a new y-axis 460 are calculated based on the greatest principal component. More specifically, the new axes shown in FIG. 6 are a linear combination of the x-axis 410 and the y-axis 420. For example, if the slope of the straight line is one (as shown in FIG. 5), the new x-axis 450 may be the sum of the x value and the y value, and the new y-axis 460 may be a difference between the x value and the y value. Or in other words, the new x- and y-axes are obtained by rotating the x-axis 420 and the y-axis 410 by 45° in the clockwise direction. In FIG. 6, the data sample 430 generally presents as one-dimensional data along the new x-axis 450, and a new small orthogonal indicator 470 is aligned with the new x-axis 450 and the new y-axis 460. In this manner, a different visual perspective of the data clusters can be provided by reducing the dimension of the data sample 430 based on principal component analysis. The different perspective may permit a user to visually distinguish data clusters to identify components of a sample.

The aspects, embodiments, and examples described in connection with FIG. 5 and FIG. 6 are exemplary, and it is contemplated that application of the aspects, embodiments, and examples to other situations will be within the scope of the present disclosure.

Figure 8:
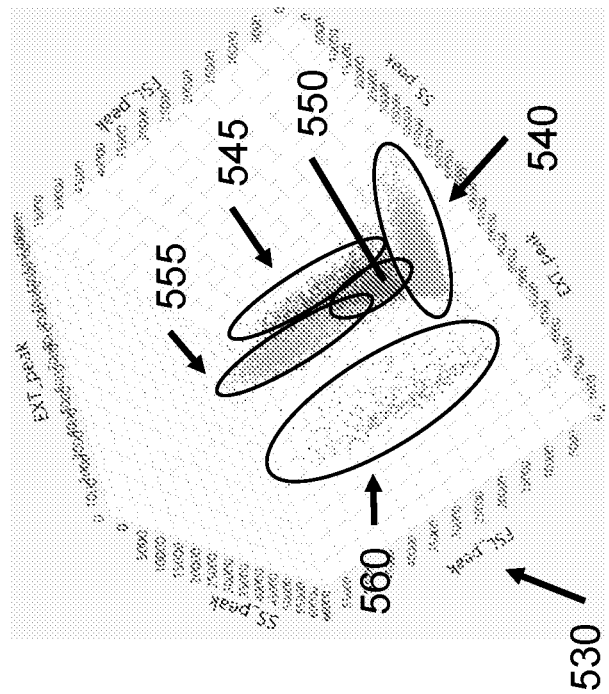
FIG. 8 shows changes in the 3D dot plot of FIG. 7 based on a principal component analysis in accordance with aspects of the present disclosure.
Figure 7:
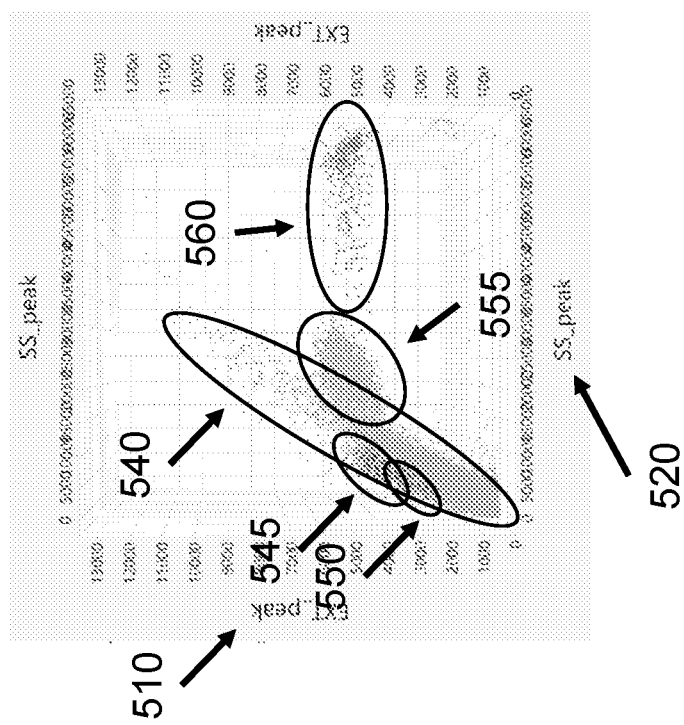
FIG. 7 shows a three-dimensional (3D) dot plot in accordance with aspects of the present disclosure.

FIGS. 7 and 8 provide another example of different perspectives of data clusters. In the example of FIG. 7 and FIG. 8, PCA may be used (as with FIG. 5 and FIG. 6) but in contrast to FIG. 6, the plotted space is rotated and is shown with the original axes rather than shown with new axes. Using flow cytometry as an example, a flow cytometry system 100 may detect extinction (EXT), low angle forward scattered light (FSL), and side scattered light (SS), among other things. FIG. 7 illustrates a three-dimensional (3D) dot plot showing five populations or data clusters 540-560 in a plot having an EXT axis 510, an SS axis 520, and a FSL axis, where the FSL axis is perpendicular to the drawing sheet and is not visualized. FIG. 8 illustrates the 3D plot showing the same five data clusters 540-560 in a plot having the same EXT axis 510, SS axis 520, and FSL axis 530, but with the 3D space rotated from that of FIG. 7. The perspective of FIG. 7 shows that the data cluster 540 substantially overlaps with data clusters 545, 550, and 555, while the perspective of FIG. 8 shows that the data clusters 540-560 are generally separated or substantially separated and minimally overlap each other. As used herein, "substantially separate" refers to and includes data clusters which are not completely separate but which can be identified as distinct data clusters based on visual inspection, statistics, data science, and/or other data or mathematical metrics.

When the perspective of FIG. 7 is changed by rotating the axes, the same data clusters 540-560 can be presented with separate or minimal overlap, as shown in the 3D plot in FIG. 8. Such rotations of the three axes may be related to the greatest principal component from the PCA. Specifically, each principal component is directly related to an eigenvalue based on the PCA, and there is a corresponding eigenvector to each principal component. The eigenvectors corresponding to the principal components may provide rotations of the three axes 510-530 so that the data clusters 540-560 can be presented in a substantially separated format as in the 3D dot plot in FIG. 8.

The aspects, embodiments, and examples described in connection with FIG. 7 and FIG. 8 are exemplary, and it is contemplated that application of the aspects, embodiments, and examples to other situations will be within the scope of the present disclosure. For example, the aspects and embodiments may be applied to systems other than flow cytometry systems.

As described above, PCA is beneficial in various circumstances, as shown in connection with FIG. 7 and FIG. 8. Additional benefits are described below in connection with FIGS. 9 and 10. The description below is described using an example of applying flow cytometry to perform hematology complete blood count. However, it is contemplated that applying the disclosed aspects, embodiments, and examples to other systems and/or applications will be within the scope of the present disclosure.

For hematology complete blood count, the sensors of the flow cytometry system 100 generally do not provide direct insight into physical properties of a sample. For example, in FIGS. 7 and 8, the data clusters are plotted with respect to light measurements, and these plots do not provide direct insight into physical properties of the components corresponding to the data clusters. Thus, the plots in FIGS. 7 and 8 may be difficult to interpret by a visual inspection. In contrast, when the axes of a plot have physical meaning or more intuitive meaning, the data clusters in the plots can be more easily interpreted to understand the meaning of the data clusters and of changes in position or population shape. For example, with respect to hematology complete blood count, plots having physical meaning or more intuitive meaning may permit cellular morphological evaluation.

In accordance with aspects of the present disclosure, data may be transformed, while maintaining the physics of the flow cytometry system 100 and the sample, to generate virtual axes that provide physical and/or more intuitive meaning. In accordance with aspects of the present disclosure, and in relation to hematology complete blood count, the virtual axes may permit morphologic interpretation of the plot.

Figure 9:
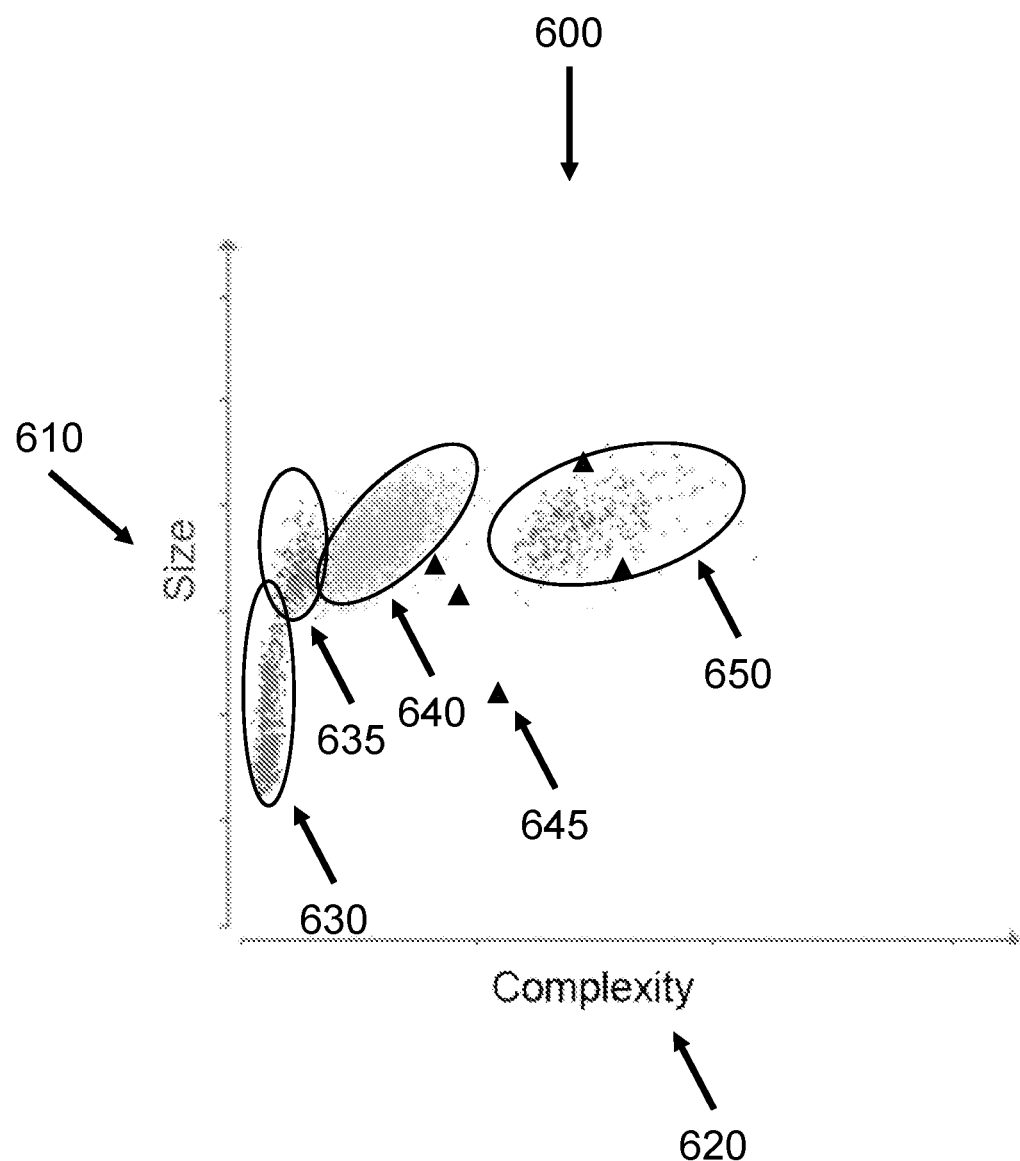
FIG. 9 is an illustrative example of a 2D dot plot in accordance with aspects of the present disclosure.
Figure 10:
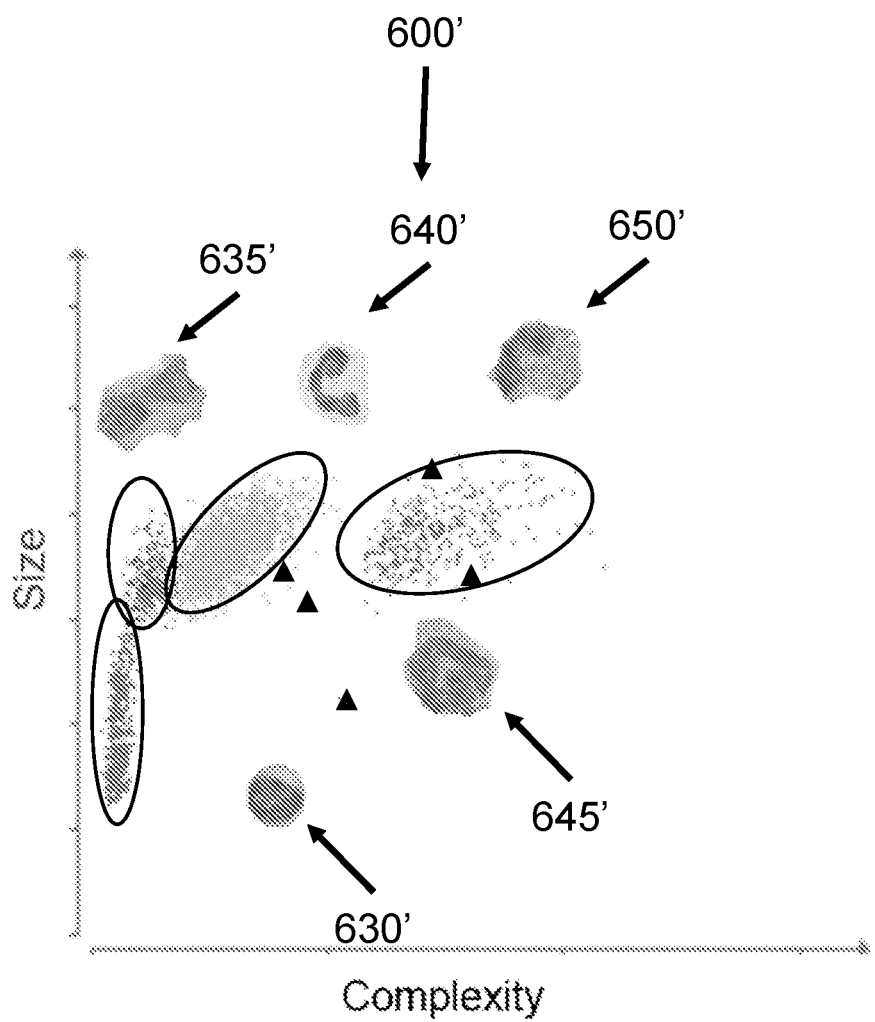
FIG. 10 is another illustrative example a 2D dot plot in accordance with aspects of the present disclosure.

Aspects of the present disclosure provide a dot plot having one axis corresponding to a physical characteristic and another axis corresponding to an optical characteristic. FIGS. 9 and 10 illustrate examples of such plots 600, 600'. The vertical axis 610 and the horizontal axis of FIGS. 9 and 10 correspond to size and scattering complexity, respectively. The size axis indicates sizes of components in the sample, and the scattering complexity axis reflects complexity of scattered light from components in the sample. In accordance with aspects of the present disclosure, Mie scattering theory is applied to estimate or determine the size and scattering complexity values of components in a sample based on the flow cytometer sensor data/metrics. For example, in embodiments, a linear combination of the data/metrics from the light sensors of the flow cytometry system 100, such as SS, FSL, FSH, EXT, and/or TOF, among others, may be used to determine size and/or scattering complexity. In aspects, the linear combination may be determined based on the eigenvector of the greatest principal component obtained from the PCA on the sensor data/metrics. In other words, scattering complexity values of data points may be calculated by taking a dot product of the sensor data/metrics and the eigenvector of the greatest principal component. With respect to hematology as an example, larger cells will have larger size and be higher on the size axis 610, and cells with more complexity (e.g., nucleus, granules, RNA/DNA, etc.) will be farther right on the complexity axis 620. FIGS. 9 and 10 are shown as 2D plots to provide an example, and higher dimensional plots are contemplated to be within the scope of the present disclosure.

The dot plot 600 of FIG. 9 corresponds to a sample of white blood cells and shows five data clusters 630-650 plotted in a plot having scatting complexity along the x-axis and size along the y-axis. Ex ante knowledge about how a component presents itself in the plot can be obtained by taking the physics of the flow cytometry system and how the component presents itself with respect to size and complexity, and then compare those with how the component looks under manual microscopy. Other alternative or additional techniques of isolating specific cell types may be used to determine where they fall in the plot in order to determine which cluster represents which cell types. In the illustrated embodiment, the first data cluster 630 includes a group of data points of lymphocytes, the second data cluster 635 includes a group of data points of monocytes, the third data cluster 640 includes a group of data points of neutrophils, the fourth data cluster 645 includes a group of data points of basophils, and the fifth data cluster 650 includes a group of data points of eosinophils. The fourth data cluster includes the smallest number of data points among the five data clusters 630-650 and spreads widely so that data points of the fourth data cluster 645 are shown in a black triangular shape and not within an enclosed oval shape. Thus, even though two black triangular shapes are included in the fifth data cluster 650, they do not belong to the fifth data cluster 650 but to the fourth data cluster 645.

Data points positioned lower along the vertical axis indicate that the size of that component is smaller. The scattering complexity of the lymphocytes (corresponding to data cluster 630) is the least among the five data clusters 630-650, while the eosinophils (corresponding to data cluster 650) have the greatest scattering complexity, as shown by the fifth data cluster 650 of the eosinophils appearing in the right-most area along the horizontal axis 620.

The sizes of monocytes, neutrophils, and eosinophils are similar to each other. Thus, the scattering complexity plays a meaningful role in distinguishing and identifying monocytes, neutrophils, and eosinophils. In a case where the scattering complexities of monocytes, neutrophils, and eosinophils may be minimal, the scale of the scattering complexity axis may be expanded or lengthened to cause the data clusters 635, 640, and 650 to appear more separate in the dot plot 600. Likewise, when the difference in size is comparatively small, the scale of the vertical axis can also be expanded or lengthened to cause the data clusters to appear more separate in the dot plot 600. In various embodiments, these expansions or lengthening of the scale of an axis can be achieved by applying transformation operations to the data points of the sample. The results is that the data clusters appear more spread out and more easily identifiable.

In various aspects, transformation may include scaling the data points. Scaling or magnification (either to make a data cluster larger or smaller) may help when the spread of the data cluster in the measured sensor space does not correlate directly with the size and scattering complexity and the data cluster is scaled so that it presents appropriately. As described above, the horizontal axis 620 or scattering complexity may be determined by the eigenvector of the greatest principal component based on the PCA. By multiplying the eigenvector by a scalar, separation of data clusters can be furthered. In a case when the distances between data clusters have a wide range (e.g., too large or too small), a decibel scale may be employed over the scattering complexity by taking logarithmic values of the data points, so that the data clusters can be presented in closer proximity in the dot plot 600. Scaling the data points is not limited to these examples but may be performed in any other ways readily appreciated by a person skilled in the art.

In embodiments, and referring again to FIGS. 7 and 8, transforming data points may include rotations around one or more axes. For example, four data clusters 540-555 overlap each other according to the perspective shown in FIG. 7, but the same four data clusters 540-555 do not generally overlap in the perspective of FIG. 8, after rotating the data points about three axes. Such rotations may correspond to the eigenvectors of the principal components. In an aspect, the rotations may be obtained by machine learning models or by manual operations.

In embodiments, and referring again to FIGS. 9 and 10, transforming data points may include translation of all or portions of the data points along the vertical axis 610, the horizontal axis 620, or a combination thereof. Translation may be helpful for moving data clusters that are overlapping in one projection but which have physically different size or scattering complexity that can be exploited by translation.

In embodiments, transforming data points may include limiting or truncating the counts of the overall number of data points. Count truncation may be performed when the number of data points of one component overwhelms with the data points of other components in the sample, such that visualization of other data clusters may be hindered. Thus, by limiting or truncating the number of data points of such a component by a particular value (generally randomly sampled but may also be specifically biased), while data points of other components are not truncated or are truncated by a different amount (or to a specified ceiling of the data cluster), visualizations of all the components in the sample can be adequately presented in the dot plot 600.

In embodiments, extrapolation may be performed during the transformation of the data points. For example, when the sensor data has data points that are saturated for a particular sensor, but sufficient information has been obtained to model the data cluster of the component by other sensors, the saturated data points may be extrapolated to add more data points to present an appropriate data cluster in the dot plot 600.

In embodiments, transformation of the data points may further include removing data points that are irrelevant to the analysis being performed. For example, when analyzing for white blood cells, the appearance of red blood cells or platelets are irrelevant and can be removed from the plot. By removing such irrelevant data points, the number of data points in the dot plot is reduced and the plot for the analysis being performed becomes easier to interpret by visual inspection.

In an aspect, the transformation may be performed independently with respect to the vertical and horizontal axes.

Based on the dot plot 600 of FIG. 9, the components of the sample can be identified with greater ease. For example, lymphocytes have the smallest size among the other components in the white blood cells, while the eosinophils have the most scattering complexity. Thus, based on the average size, the lymphocytes can be identified to be in the first data cluster 630 and the eosinophils can be identified to be in the fifth data cluster 650. Monocytes are generally larger than lymphocytes and have the least complexity, similar to the lymphocytes as those two cells are commonly grouped into a category called mononuclear cells. Neutrophils are similar in size to monocytes and are more complex since the nucleus is segmented and causes a different light scattering. Eosinophils and basophils are similar in size to neutrophils but have additional complexity. Thus, based on the size and scattering complexity of the data clusters, corresponding components in the white blood cells can be visually identified from the plot 600.

In accordance with aspects of the present disclosure, and based on visual interpretation of the dot plot 600, abnormality in the components of the sample can be identified with greater ease. Continuing with the example of white blood cells, morphological changes to the components results in identifiable effects on the plot. For example, segmented nucleus of the neutrophil reduces its scattering complexity as the segments have fewer scattering features, and the corresponding data cluster shifts to the left on the scattering complexity axis and potentially up in size. As another example, for lymphocytes that have become reactive, the size of the reactive lymphocytes becomes larger than the size of normal lymphocytes, while the scattering complexity of normal and reactive lymphocytes are substantially the same. Thus, when the first data cluster 630 shows a relatively long distribution along the vertical axis 610, the lymphocytes can be relatively easily interpreted as having abnormalities or being reactive.

As another example, if neutrophils experience certain morphological changes, such as "toxic neutrophils" where the bone marrow releases neutrophils too quickly, scattering complexity of neutrophils shifts to the left. Thus, abnormality in neutrophils can be identified based on shifts in scattering complexity.

For another example, basophils form about 0.5% to about 1% of total white blood cells. When allergic reactions occur in the body, the number of basophils increases in the white blood cells. Thus, based on changes in the count of the fourth data cluster 645, abnormality in basophils can be identified.

Thus, changes in size or scattering complexity of the data clusters for a white blood cell sample can signify presence of abnormalities. In various aspects, reference data clusters in the dot plot, which include normal ranges of sizes and scattering complexities, may function as a reference in identifying abnormality in the white blood cells. The sample is not limited to blood cells but can include any mixtures or compounds for which changes in counts or shifts in size and/or scattering complexity indicate the presence of abnormality. Accordingly, the aspects, embodiments, and examples described with respect to FIGS. 9 and 10 are applicable to other samples, contexts, or situations not expressly described herein.

In various aspects, representative images may be displayed in the dot plot 600' near the corresponding data clusters, as shown in FIG. 10. For example, a representative image of lymphocytes 630' is displayed next to the first data cluster 630, a representative image 635' of monocytes is displayed near the second data cluster 635, a representative image 640' of neutrophils is displayed near the third data cluster 640, a representative image 645' of basophils is displayed near the fourth data cluster 645, and a representative image of eosinophils is displayed near the fifth data cluster 650. By displaying the representative images 630'-650', the five components in the white blood cells can be more easily identified.

Figure 11:
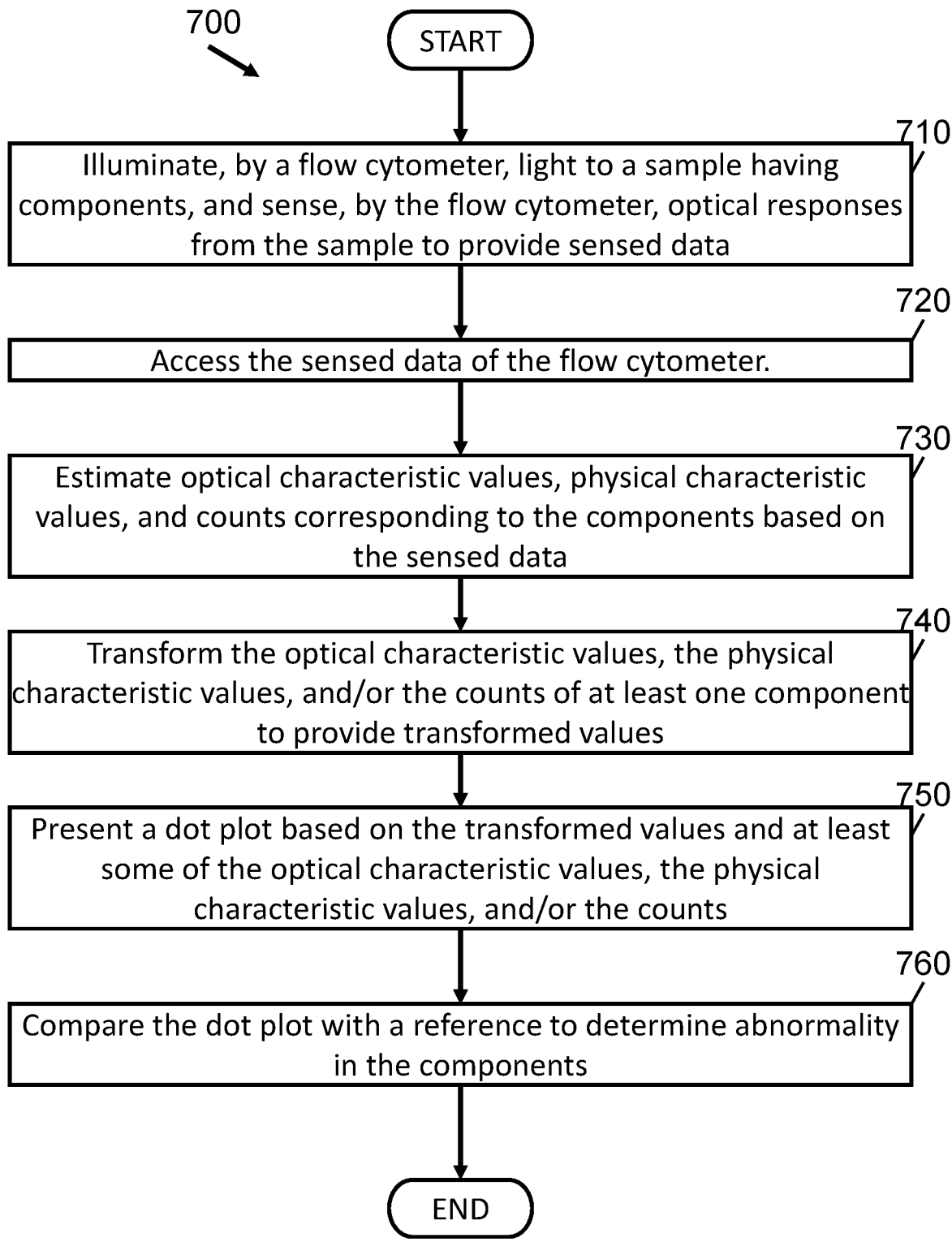
FIG. 11 is a flow chart of a flow cytometry method in accordance with aspects of the present disclosure.

FIG. 11 shows a flowchart illustrating a method 700 for presenting a dot plot and identifying components in the sample according to aspects of the present disclosure. When a sample in a fluid solution is contained in a transparent container (e.g., the cuvette 115 of FIG. 1) and individual components move forward, a flow cytometer illuminates a beam of light (e.g., laser beam) to the individual cells or components in the sample at step 710. As the light beam strikes each component, the light is absorbed and scattered. The type of scattered light produced may depend on the degree of granularity, the size of the component, etc. These optical responses from the components are sensed by the flow cytometer as sensor data at step 710.

The sensed data is accessed at step 710, and the sensed data is analyzed to estimate optical characteristic values, physical characteristic values, and counts corresponding to each component at step 730. The optical characteristic values, in some embodiments, include level of absorption or scattering or include complexity of scattering, and the physical characteristics include size.

At step 740, some or all of the optical characteristic values, the physical characteristic values, and/or the counts are transformed to provide transformed values. The transformation, in embodiments, includes one or more of rotation, magnification, translation, truncation, and/or extrapolation, among other transformations. Examples of transformations are described farther below.

At step 750, a dot plot is presented based on the transformed values and based on at least some of the optical characteristic values, the physical characteristic values, and/or the counts. The dot plot may be a plot in two dimensions or more than two dimension. One axis of the dot plot corresponds to the optical characteristic values, and another axis of the dot plot corresponds to the physical characteristic values. The dot plot includes data clusters that correspond to the components in the sample. In embodiments, the physical characteristic values are indicative of size of components, and the optical characteristic values are indicative of scattering complexity. In such embodiments, the data clusters in the dot plot may be more easily interpreted according to where they fall with respect to size and scattering complexity.

The transformations at step 740 may help the data clusters in the dot plot become separated or substantially separated. In embodiments, two or more data clusters may be rotated to cause the data clusters to be separated or substantially separated in the dot plot. Or, in other words, when an overlapping area between two or more data clusters is greater than a predetermined threshold according to one perspective, the axes are rotated to change the perspective so that the overlapping area is less than or equal to the first predetermined threshold according to the new perspective, as shown in FIGS. 7 and 8. Such rotations may be determined by machine learning models, manual trial and error, or the eigenvectors of the principal components according to the PCA.

In circumstances in which two or more data clusters overlap, the size and/or scattering complexity can be magnified so that the overlapping area can be reduced below or equal to the first predetermined threshold, in some embodiments.

In some embodiments, in circumstances in which two or more data clusters overlap according to one perspective but do not overlap according to another perspective, one or more data clusters may be translated without damaging integrity of the data clusters.

In circumstances in which one component in the sample is substantially larger in counts than another component, the count of the one component may be truncated while maintaining general trend of the data clusters.

In some embodiments, if a portion of the sensor data of one component is saturated at the maximum sensor output value, but other information that is not saturated would be sufficient to model the data cluster, then the data cluster may be extrapolated based on such other data to add more data points for display in the dot plot.

At step 760, the dot plot is compared with reference data cluster dot plots. When one data cluster moves along one axis (e.g., the size) or shifts along another axis (e.g., scattering complexity) in the dot plot with respect to the corresponding reference data cluster in the reference dot plot, the component showing the changes or shifts may be determined to have abnormality.

Further, since data clusters of all components are displayed in one dot plot, a user reviewing the dot plot can make a comprehensive diagnosis or prognosis on all components in the sample with ease.

The aspects disclosed herein are examples of the disclosure and may be embodied in various forms. For instance, although certain aspects herein are described as separate aspects, each of the aspects herein may be combined with one or more of the other aspects herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical components throughout the description of the figures.

The phrases "in an aspect," "in aspects," "in various aspects," "in some aspects," "in various aspects," or "in other aspects" may each refer to one or more of the same or different aspects in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Any of the herein described methods, programs, algorithms, or codes may be converted to, or expressed in, a programming language or computer program. The terms "programming language" and "computer program," as used herein, each include any language used to specify instructions to a computer or processor, and include (but is not limited to) the following languages and their derivatives: Assembler, Basic, Batch files, BCPL, C, C+, C++, Delphi, Fortran, Java, JavaScript, machine code, Matlab, operating system command languages, Pascal, Perl, PL1, Python, scripting languages, Visual Basic, metalanguages which themselves specify programs, and all first, second, third, fourth, fifth, or further generation computer languages. Also included are database and other data schemas, and any other metalanguages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The aspects described with reference to the attached drawing figures are presented only to demonstrate certain examples of the disclosure. Other components, steps, methods, and techniques that are insubstantially different from those described above and/or in the appended claims are also intended to be within the scope of the disclosure.

The systems described herein may also utilize one or more controllers or processors to receive various information and transform the received information to generate an output. The controller or processor may include any type of computing device, computational circuit, or any type of processing circuit capable of executing a series of instructions that are stored in a memory. The controller or processor may include multiple processing units and/or multicore central processing units (CPUs) and may include any type of processing device, such as a microprocessor, digital signal processor, microcontroller, programmable logic device (PLD), field programmable gate array (FPGA), application specific integrated circuit (ASIC), or the like. The controller or processor may be located within a device or system at an end-user location, may be located within a device or system at a manufacturer or servicer location, or may be a cloud computing processor located at a cloud computing provider. The controller or processor may also include and/or access a memory and/or a processor-readable medium to store data and/or instructions that, when executed by the one or more processors, causes the one or more processors to perform one or more methods and/or algorithms.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The aspects described with reference to the attached drawing figures are presented only to demonstrate certain examples of the disclosure. Other components, steps, methods, and techniques that are insubstantially different from those described above and/or in the appended claims are also intended to be within the scope of the disclosure.

What is claimed:

1. A method for presenting flow cytometry data, the method comprising:

accessing sensed data of a flow cytometer used to sense optical responses from a sample, the sample comprising a plurality of components;

estimating optical characteristic values, physical characteristic values, and counts of the plurality of components based on the sensed data;

transforming at least some of the optical characteristic values, the physical characteristic values, or the counts, of at least one of the plurality of components, by at least one of rotating or translating, to provide transformed values; and presenting a two-dimensional (2D) dot plot based on the transformed values and based on at least some of the optical characteristic values, the physical characteristic values, and the counts, of the plurality of components, the 2D dot plot having a first axis corresponding to the optical characteristic values and a second axis corresponding to the physical characteristic values, wherein the 2D dot plot includes data clusters corresponding to the plurality of components, and wherein the transforming comprises truncating the count of at least one of the plurality of components to provide at least some of the transformed values, the truncating resulting in at least some of the data clusters being separated or substantially separated in the 2D dot plot.

2. The method according to claim 1, wherein the physical characteristic values are indicative of size and the optical characteristic values are indicative of scattering complexity.

3. The method according to claim 1, further comprising:
comparing the data clusters in the 2D dot plot with reference data clusters to determine presence of abnormality in the plurality of components.

4. The method according to claim 1, wherein the data clusters corresponding to the plurality of components are substantially separated from each other in the 2D dot plot.

5. The method according to claim 1, wherein the transforming comprises:
magnifying at least some of the optical characteristic values or the physical characteristic values to provide at least some of the transformed values, the magnifying resulting in at least some of the data clusters being separated or substantially separated in the 2D dot plot.

6. The method according to claim 1, wherein the transforming comprises:
rotating at least some of the optical characteristic values about at least one of the first axis or the second axis to provide at least some of the transformed values, the rotating resulting in at least some of the data clusters being separated or substantially separated in the 2D dot plot.

7. The method according to claim 1, wherein the transforming comprises:
translating at least some of the optical characteristic values or the physical characteristic values along at least one of the first axis or the second axis to provide at least some of the transformed values, the translating resulting in at least some of the data clusters being separated or substantially separated in the 2D dot plot.

8. The method according to claim 1, wherein the transforming comprises performing a principal component analysis on at least some of the optical characteristic values, the physical characteristic values, or the counts.

9. A system for presenting flow cytometry data, the system comprising:
a processor; and
a memory including instructions stored thereon which, when executed by the processor, cause the system to:

access sensed data of a flow cytometer used to sense optical responses from a sample, the sample comprising a plurality of components;

estimate optical characteristic values, physical characteristic values, and counts of the plurality of components based on the sensed data;

transform at least some of the optical characteristic values, the physical characteristic values, or the counts, of at least one of the plurality of components, by at least one of rotation or translation, to provide transformed values; and present a two-dimensional (2D) dot plot based on the transformed values and based on at least some of the optical characteristic values, the physical characteristic values, and the counts, of the plurality of components, the 2D dot plot having a first axis corresponding to the optical characteristic values and a second axis corresponding to the physical characteristic values, wherein the 2D dot plot includes data clusters corresponding to the plurality of components, and wherein the transform comprises truncating the count of at least one of the plurality of components to provide at least some of the transformed values, the truncating resulting in at least some of the data clusters being separated or substantially separated in the 2D dot plot.

10. The system according to claim 9, wherein the physical characteristic values are indicative of size and the optical characteristic values are indicative of scattering complexity.

11. The system according to claim 9, wherein the instructions, when executed by the processor, further cause the system to:
compare the data clusters in the 2D dot plot with reference data clusters to determine presence of abnormality in the plurality of components.

12. The system according to claim 9, wherein the data clusters corresponding to the plurality of components are substantially separated from each other in the 2D dot plot.

13. The system according to claim 9, wherein in the transforming, the instructions, when executed by the processor, cause the system to:
magnify at least some of the optical characteristic values and the physical characteristic values to provide at least some of the transformed values, the magnifying resulting in at least some of the data clusters being separated or substantially separated in the 2D dot plot.

14. The system according to claim 9, wherein in the transforming, the instructions, when executed by the processor, cause the system to:
rotate at least some of the optical characteristic values about at least one of the first axis or the second axis to provide at least some of the transformed values, the rotating resulting in at least some of the data clusters being separated or substantially separated in the 2D dot plot.

15. The system according to claim 9, wherein in the transforming, the instructions, when executed by the processor, cause the system to:
translate at least some of the optical characteristic values or the physical characteristic values along at least one of the first axis or the second axis to provide at least some of the transformed values, the translating resulting in at least some of the data clusters being separated or substantially separated in the 2D dot plot.

16. The system according to claim 9, wherein in the transforming, the instructions, when executed by the processor, cause the system to perform a principal component analysis on at least some of the optical characteristic values, the physical characteristic values, or the counts.

17. A processor-readable medium storing instructions which, when executed by a processor, causes performance of a method comprising:
- accessing sensed data of a flow cytometer used to sense optical responses from a sample, the sample comprising a plurality of components;
- estimating optical characteristic values, physical characteristic values, and counts of the plurality of components based on the sensed data;
- transforming at least some of the optical characteristic values, the physical characteristic values, or the counts, of at least one of the plurality of components, by at least one of rotating or translating, to provide transformed values; and
- presenting a two-dimensional (2D) dot plot based on the transformed values and based on at least some of the optical characteristic values, the physical characteristic values, and the counts, of the plurality of components, the 2D dot plot having a first axis corresponding to the optical characteristic values and a second axis corresponding to the physical characteristic values,
- wherein the 2D dot plot includes data clusters corresponding to the plurality of components, and
- wherein the transforming comprises truncating the count of at least one of the plurality of components to provide at least some of the transformed values, the truncating resulting in at least some of the data clusters being separated or substantially separated in the 2D dot plot.

18. The processor-readable medium according to claim 17, wherein the physical characteristic values are indicative of size and the optical characteristic values are indicative of scattering complexity.

* * * * *